(12) United States Patent
Thenuwara et al.

(10) Patent No.: US 9,561,361 B2
(45) Date of Patent: Feb. 7, 2017

(54) ATRAUMATIC ELECTRODE LEAD

(75) Inventors: Chuladatta Thenuwara, Castaic, CA (US); Rosa Gallego, Sylmar, CA (US); Lidia Vasquez, Palmdale, CA (US); Mark B. Downing, Valencia, CA (US)

(73) Assignee: Advanced Bionics AG, Staefa (CH)

(*) Notice: Subject to any disclaimer, the term of this patent is extended or adjusted under 35 U.S.C. 154(b) by 50 days.

(21) Appl. No.: 14/345,596

(22) PCT Filed: Oct. 7, 2011

(86) PCT No.: PCT/US2011/055418
§ 371 (c)(1),
(2), (4) Date: Mar. 18, 2014

(87) PCT Pub. No.: WO2013/052066
PCT Pub. Date: Apr. 11, 2013

(65) Prior Publication Data
US 2014/0343657 A1 Nov. 20, 2014

(51) Int. Cl.
*A61N 1/05* (2006.01)
*A61N 1/36* (2006.01)
*H04R 25/00* (2006.01)
*H04R 31/00* (2006.01)

(52) U.S. Cl.
CPC ......... *A61N 1/0541* (2013.01); *A61N 1/36032* (2013.01); *H04R 25/00* (2013.01); *H04R 31/006* (2013.01); *H04R 2225/67* (2013.01); *H04R 2231/003* (2013.01); *Y10T 29/4922* (2015.01); *Y10T 29/49213* (2015.01)

(58) Field of Classification Search
CPC ........ A61N 1/05; A61N 1/0541; H04R 25/00; H04R 31/00; H04R 31/006; H04R 2225/67; H04R 2231/003

USPC .......................................................... 607/137
See application file for complete search history.

(56) References Cited

U.S. PATENT DOCUMENTS

| | | | |
|---|---|---|---|
| 4,033,355 A | 7/1977 | Amundson | |
| 4,643,202 A | 2/1987 | Roche | |
| 5,658,327 A | 8/1997 | Altman | |
| 5,823,955 A * | 10/1998 | Kuck | A61B 18/1492 600/374 |
| 5,837,007 A | 11/1998 | Altman | |
| 6,477,396 B1 * | 11/2002 | Mest | A61B 18/1492 600/374 |

(Continued)

OTHER PUBLICATIONS

Xu, Shi-Ang et al.; "Evaluation of expandable leadwires for paediatric cochlear implants"; Mar. 1993; American Journal of Otology; vol. 14(2); pp. 151-160.

*Primary Examiner* — Christopher D Koharski
*Assistant Examiner* — Roland Dinga
(74) *Attorney, Agent, or Firm* — Fabian VanCott; Steven Nichols

(57) ABSTRACT

A cochlear implant includes a processor, an array of electrodes disposed along a flexible body and a lead body connecting the processor to the array of electrodes. The lead body includes a first tube having a first outside diameter, a second tube having a second outside diameter smaller than the first diameter, a portion of the second tube being disposed within the first tube, and wires passing through the first tube and the second tube, the wires comprising a helically coiled portion. A method for forming a lead body is also provided.

21 Claims, 8 Drawing Sheets

(56) References Cited

U.S. PATENT DOCUMENTS

| | | | |
|---|---|---|---|
| 2003/0014088 A1* | 1/2003 | Fang | A61N 1/36017 |
| | | | 607/48 |
| 2007/0055091 A1* | 3/2007 | Lau | A61F 2/2481 |
| | | | 600/16 |
| 2007/0067008 A1 | 3/2007 | Scheiner et al. | |
| 2007/0106360 A1 | 5/2007 | Gibson et al. | |
| 2009/0248117 A1* | 10/2009 | Nippoldt | A61B 5/02152 |
| | | | 607/60 |
| 2010/0305676 A1 | 12/2010 | Dadd et al. | |
| 2011/0022145 A1* | 1/2011 | Beerling | A61N 1/0541 |
| | | | 607/137 |
| 2011/0054581 A1 | 3/2011 | Desai et al. | |
| 2011/0066195 A1* | 3/2011 | Alexander | A61N 1/0534 |
| | | | 607/2 |
| 2011/0087299 A1* | 4/2011 | Ameri | A61N 1/056 |
| | | | 607/2 |
| 2011/0245887 A1 | 10/2011 | Klardie et al. | |

* cited by examiner

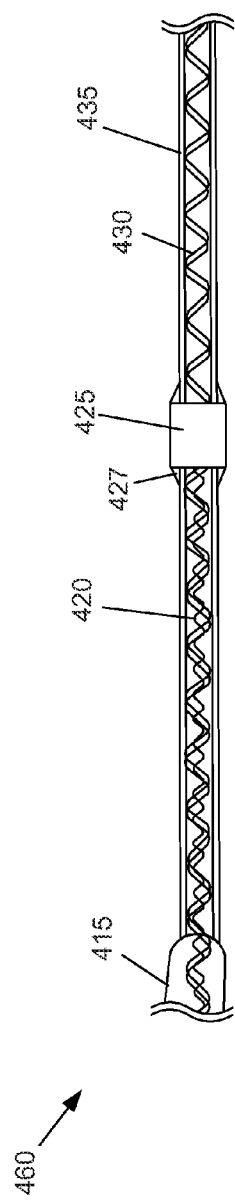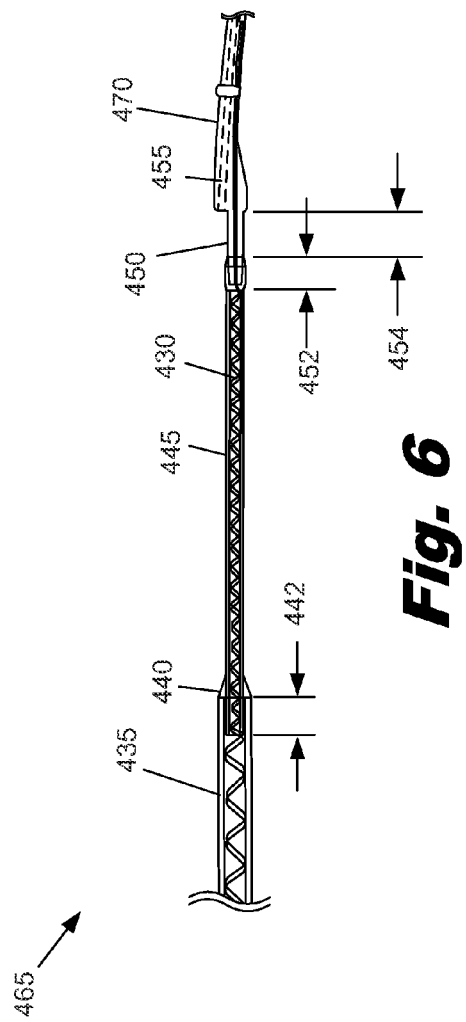

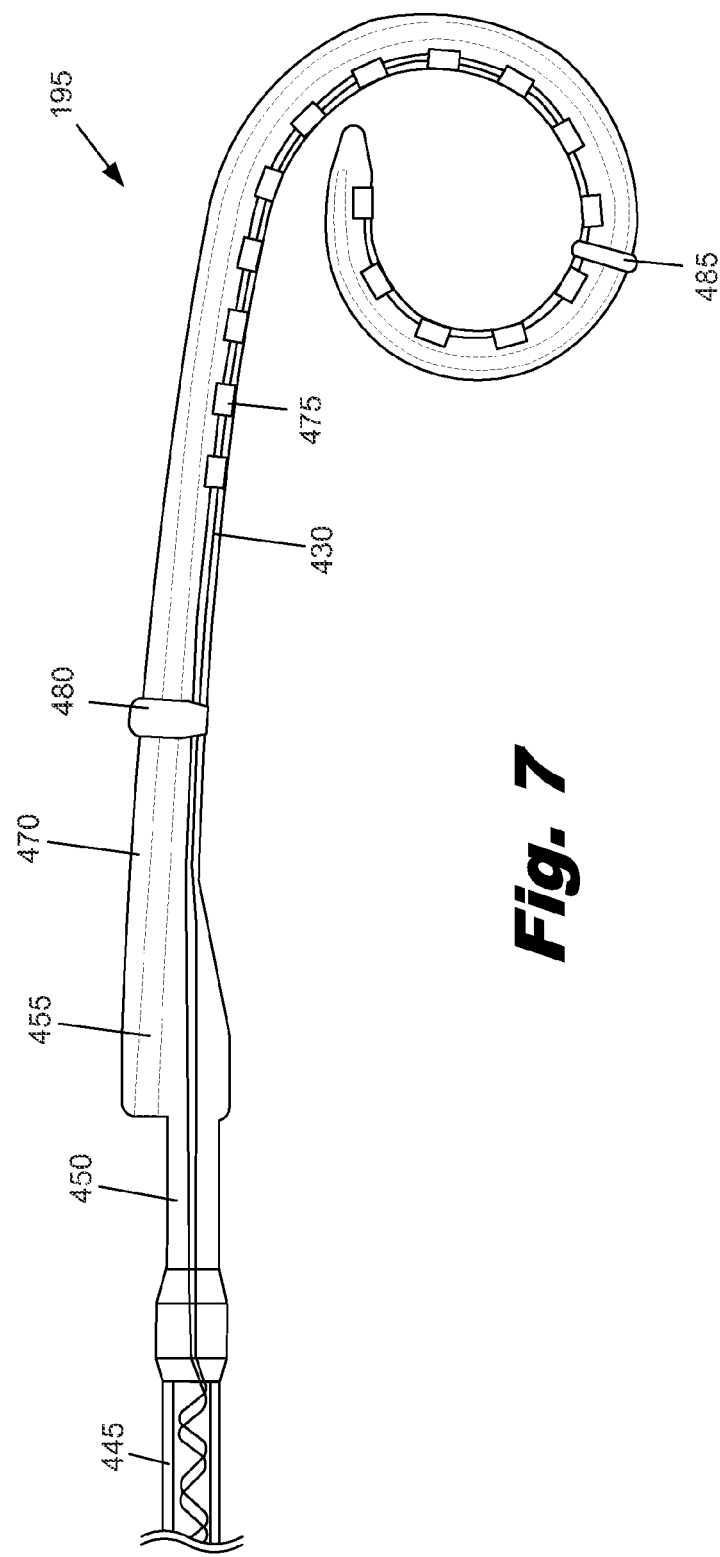

ATRAUMATIC ELECTRODE LEAD

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the natural mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear haft cells that normally transduce acoustic energy into electrical activity in the connected auditory nerve cells.

The implantation of the cochlear prosthesis involves the insertion of an electrode array into the cochlea of the patient. The interior structures of the cochlea can be delicate and sensitive to forces generated by the insertion of the electrode array. Minimizing trauma to the cochlea during implantation improves patient outcomes and preserves residual hearing.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 5 is a side view of a proximal segment of an atraumatic electrode lead, according to one example of principles described herein.

FIG. 6 is a side view of a distal segment of an atraumatic electrode lead, according to one example of principles described herein.

FIG. 7 is a side view of a cochlear electrode array, according to one example of principles described herein.

Throughout the drawings, identical reference numbers designate similar, but not necessarily identical, elements.

DETAILED DESCRIPTION

As mentioned above, individuals with hearing loss can be assisted by a number of hearing devices, including cochlear implants. The cochlear implant includes a cochlear lead that is surgically implanted into the patient. The distal portion of the lead contains a number of electrodes that electrically stimulate the auditory nerve system. This electrode array is typically constructed out of biocompatible silicone, platinum-iridium wires, and platinum electrodes. To place the lead of a cochlear implant, the distal (or apical) portion of a cochlear lead is pushed through an opening into the cochlea. To reduce trauma and hearing loss, it is desirable that the cochlear lead be inserted into the patient with minimal force and reduced contact with the interior structures in the cochlea.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

As used in the specification and appended claims, the term "distal" refers to portions or components that are farther away from the cochlear implant processor and the surgeon implanting the cochlear device. The term "proximal" refers to portions or components that are closer to the processor and/or the surgeon implanting the cochlear device.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of the current. Consequently, stimulation at one contact site tends to selectively activate those spiral ganglion cells and their auditory nerve fibers that are closest to that electrode.

Figure 1:
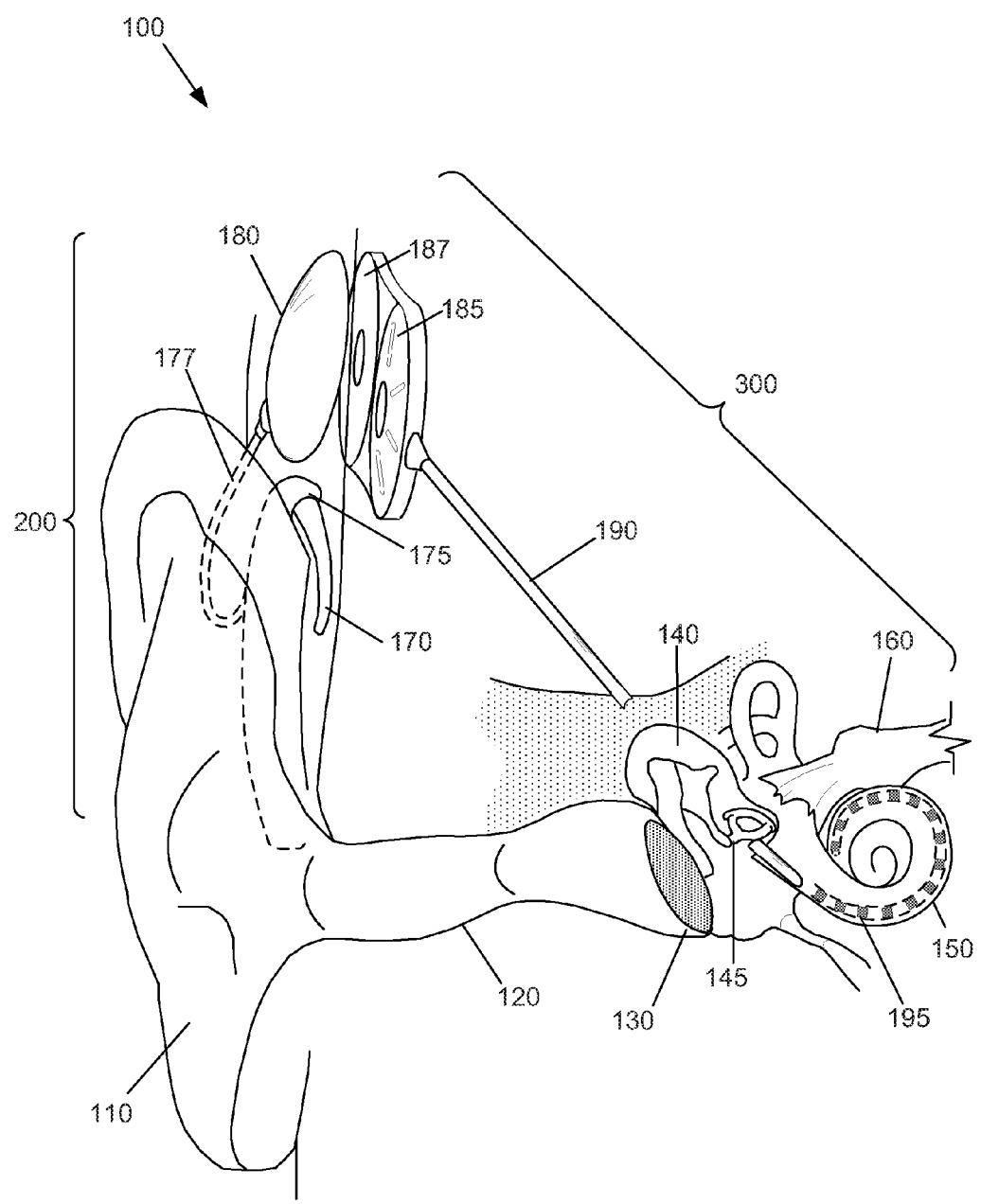
FIG. 1 is an illustrative diagram showing a cochlear implant system in use, according to one example of principles described herein.

FIG. 1 is a diagram showing an illustrative cochlear implant system (100) having a cochlear implant (300) with an electrode array (195) that is surgically placed within the patient's cochlea (150). Ordinarily, sound enters the external ear, or pinna, (110) and is directed into the auditory canal (120) where the sound wave vibrates the tympanic membrane (130). The motion of the tympanic membrane (130) is amplified and transmitted through the ossicular chain (140), which includes three bones in the middle ear. The third bone of the ossicular chain (140), the stapes (145), contacts the outer surface of the cochlea (150) and causes movement of the fluid within the cochlea (150). Cochlear hair cells respond to the fluid-borne vibration in the cochlea (150) and trigger neural electrical signals that are conducted from the cochlea to the auditory cortex by the auditory nerve (160).

As indicated above, the cochlear implant (200, 300) is a surgically implanted electronic device that provides a sense of sound to a person who is profoundly deaf or severely hard of hearing. The cochlear implant (200, 300) operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission.

The internal components (300) include an internal processor (185), an antenna (187), and a cochlear lead (190) having an electrode array (195) at its distal end. The internal processor (185) and antenna (187) are secured beneath the user's skin, typically above and behind the external ear (110). The antenna (187) receives signals and power from the transmitter (180). The internal processor (185) receives these signals and performs one or more operations on the signals to generate modified signals. These modified signals are then sent along a number of signal wires that pass through the cochlear lead (190) and are individually connected to the electrodes in the electrode array (195). The electrode array (195) is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
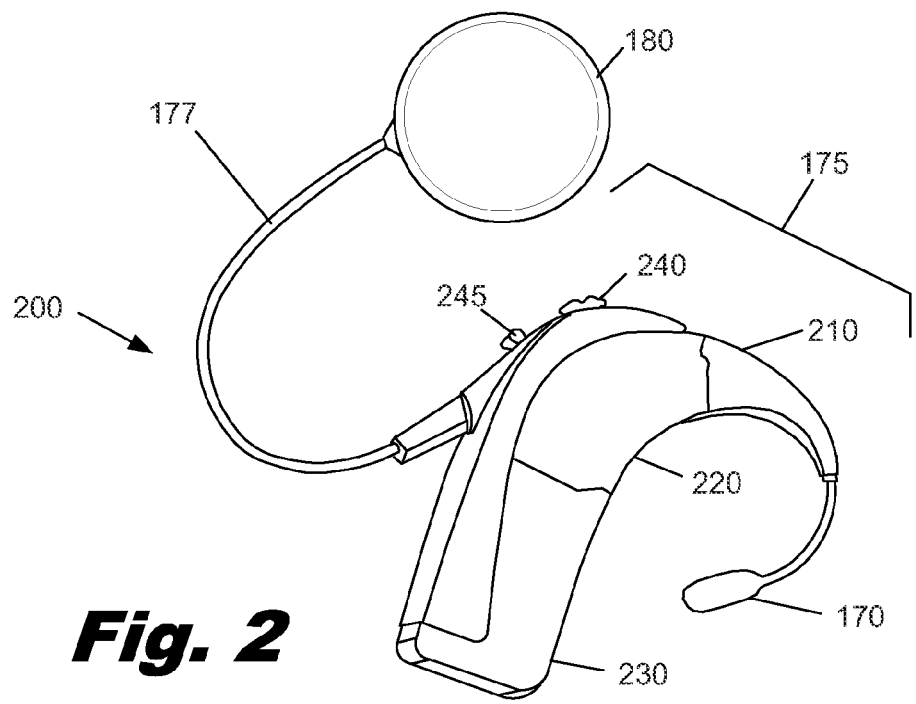
FIG. 2 is a diagram showing external components of an illustrative cochlear implant system, according to one example of principles described herein.

FIG. 2 is an illustrative diagram showing a more detailed view of the external components (200) of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant (300) by electromagnetic transmission.

Figure 3:
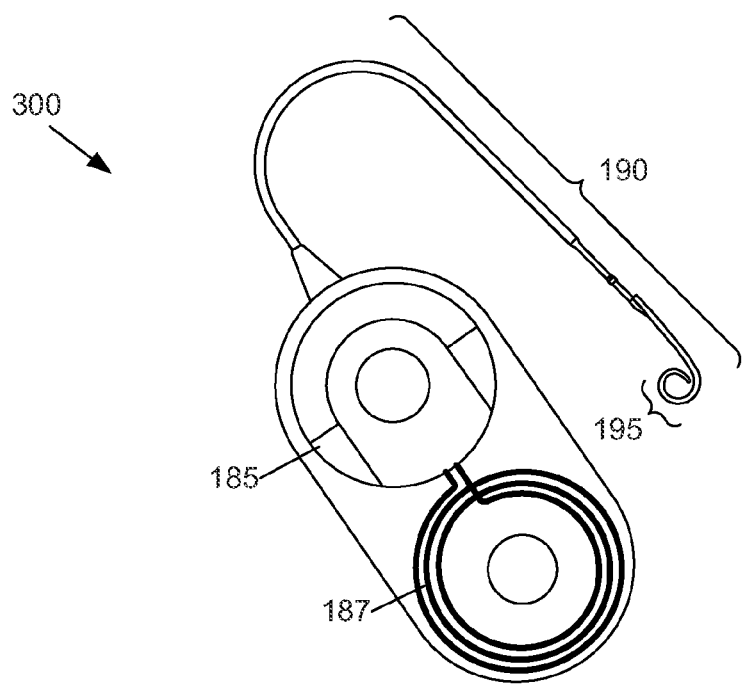
FIG. 3 is a diagram showing the internal components of an illustrative cochlear implant system, according to one example of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the external ear (110), with the cochlear lead (190) connecting the internal processor (185) to the electrode array (195) within the cochlea. As discussed above, the antenna (187) receives signals from the transmitter (180) and sends the signals to the internal processor (185). The internal processor (185) modifies the signals and passes them along the appropriate wires to activate one or more of the electrodes within the electrode array (195). This provides the user with sensory input that is a representation of external sound waves sensed by the microphone (170).

Figure 4:
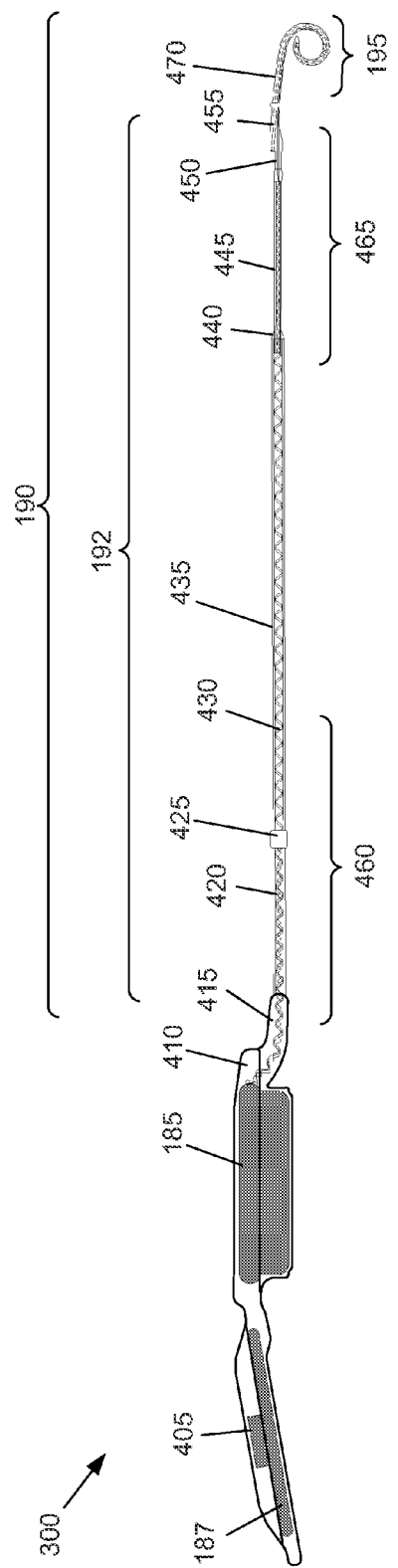
FIG. 4 is a side view of internal components of an illustrative cochlear implant system, according to one example of principles described herein.

FIG. 4 is a diagram of implanted components (300) of a cochlear implant. As discussed above, the implanted components (300) include an antenna (187) and a processor (185). In the center of the antenna (405) is a magnet (405) that is designed to center and hold the transmitter (180, FIG. 1) in place. The antenna (187), magnet (405), and processor (185) are encapsulated by an overcoat (410). The cochlear lead (90) includes a lead body (192) and an electrode array (195). The lead body (192) mechanically and electrically connects the electrode array (195) to the processor (185). In this implementation, the lead body (192) includes a first larger diameter tube (435) and a second smaller diameter tube (445). The length of the lead body (192) may vary according to the cochlear implant design, surgical procedure, and patient. For example, the lead body (192) may have a length of 70 to 100 millimeters. In one specific implementation, the lead body (192) has a length of about 85 millimeters measured from the processor overmolding (410) to the flexible body (470).

Helically coiled wires (420, 430) pass through the large and small diameter tubes (435, 445). Helically coiled signal wires (430) electrically connect the electrode array (195) to the processor (185). A second helically coiled wire (420) connects the processor (185) to a ring electrode (425) located around the large diameter tube (435). The second helically coiled wire (420) may have a variety of configurations. For example the second helically coiled wire (420) may be formed from nine strand twisted or braided platinum wire coated with polytetrafluoroethylene (PTFE). The ring electrode (425) can be used as a common ground or for Neural Response Imaging (NRI) for the processor (185) and its internal electronics. The signal wires (430) carry voltage pulses to the active electrodes in the electrode array (195).

The large diameter tube (430) extends out of the strain relief (415). In some embodiments the tube (430) may extend through the strain relief (415) to the processor (185). The second smaller diameter tube (445) is mechanically connected to the large diameter tube (430) by placing a portion of the small diameter tube (445) inside the large diameter tube (445) and creating a tapered transition (440)

between the two tubes. The small diameter tube (445) is mechanically connected to the flexible body (470) by placing a transition tube (450) into the interior or the small diameter tube (445). The transition tube (450) is molded into the flexible body (140). In one example, the transition tube (450) has a Shore A hardness of 70.

FIGS. 5, 6, and 7 show up close views of portions of the implanted components (300) illustrated in FIG. 4. FIG. 5 shows the proximal portion (460) of the lead body. FIG. 6 shows the transition portion (465) between the large diameter tube (430), the small diameter tube (445), transition tube (450) and the flexible body (470). FIG. 7 shows the distal end the small diameter tube (445), the transition tube (450) and the electrode array (195).

Now referring to FIG. 5, a proximal portion (460) of the lead body includes the large diameter tube (430) that has an outer diameter which is less than 2 millimeters in diameter. In one implementation, the large diameter tube (430) may have an outside diameter of between 1 to 2 millimeters and an inside diameter of between 0.5 and 1 millimeters. For example, the large diameter tube may have an outside diameter of approximately 1.25 millimeters and an inside diameter of approximately 0.7 millimeters. The large diameter tube (430) may be formed from a variety of flexible biocompatible materials. In this implementation, the large diameter tube (430) is formed from silicone with a Shore A hardness of approximately 30 to 70. The dimensions given above and other dimensions of flexible materials in the specification are nominal unstressed dimensions. When placed under stress, biocompatible elastomeric polymers such as silicone have the capacity to stretch, compress or otherwise conform. For example, a silicone tube within an unstressed inside diameter of 0.7 millimeters may be placed over an object with a diameter that is greater than 0.7 millimeters. The silicone tube expands to accommodate the larger object and the stretched inside diameter of the silicone tube is greater than 0.7 millimeters.

The large diameter tube (430) is molded into the strain relief (415), which secures the large diameter tube (430) to the processor (185, FIG. 4). As discussed above, the signal wires (430) pass from the processor, into the large diameter tube (430) and through its length. The ground wire (420) is also helically coiled and passes through the center of the helically coiled signal wires (430). In one embodiment, the ground wire (420) is a multi-strand wire. The ground wire (420) passes out of an opening in the sidewall of the large diameter tube (430) and is electrically connected to the extra-cochlear ring electrode (425) disposed over the large diameter tube (430). As discussed above, the ring electrode (425) serves as a ground for the processor and its internal electronics. The ground wire (420) connects the ring electrode to the processor (185, FIG. 4). Because the ring electrode (425) serves as the ground for all of the electrodes, ground wire (420) may need to carry a substantial amount of current. Consequently, the ground wire (420) may be significantly larger in diameter than the signal wires. To reduce the stiffness of the larger diameter ground wire (420) it may be multi-strand and formed into a helix. The strain relief (415) is molded over the large diameter tube (435) and secures it to the processor (185, FIG. 4). The large diameter tube (435) is backfilled with silicone to encapsulate the signal wire bundle (430) and ground wire (420).

Silicone may be used to form tapers (427) on either side of the ring electrode (425). The tapers (427) may provide a number of advantages, include smoothing the profile of the large diameter tube (435), securing the ring electrode (425) in place, and reducing the potential for kinking of the large diameter tube (435).

FIG. 6 shows the small diameter tube (445) joining the large diameter tube (435) to the transition tube (450). In one implementation, the small diameter tube (445) is formed from silicone with a Shore A hardness between 50 and 70 and has an outside diameter larger than the inside diameter of the large diameter tube (435). For example, the small diameter tube (445) may have an outside diameter of 0.75 millimeters, an inside diameter of 0.35 millimeters, and a Shore A hardness of 70. When the small diameter tube (445) is placed within the large diameter tube (435), the large diameter tube (435) compresses the small diameter tube (445) and holds it securely in place. In one example, the overlap (442) between the large diameter tube (435) and the small diameter tube (445) is at least 1 millimeter. When silicone is injected into the tubes, it flows through the overlapping portion and forms an additional bond between the large diameter tube (435) and the small diameter tube (445).

A tapered transition (440) between the large diameter tube (435) and the small diameter tube (445) can be formed using silicone which cures to a Shore A hardness of approximately 25. This tapered transition (440) can serve a number of purposes, including smoothing the transition between the large diameter tube (435) and small diameter tube (445), sealing the joint, and stiffening the joint. The transition can also ensure that there are no stress concentrations and undesirable bending or kinking near the joint.

The other end of the small diameter tube (445) passes over the transition tube (450). As described above, the transition tube (450) is molded into the flexible body (470). In one embodiment, the transition tube (450) has an outside diameter less than 1 millimeter and inside diameter of less than 0.5 millimeters. For example, the transition tube (450) may have an outside diameter of 0.65 millimeters and an inside diameter of 0.30 millimeters. The small diameter tube (445) has an inside diameter of which is smaller than the outside diameter of the transition tube (450). Consequently, when the small diameter tube (445) is placed over the transition tube (450), the inside diameter of the smaller diameter tube (445) expands to pass over the outside diameter of the transition tube (450). The outside diameter of the transition tube (450) may also shrink from the pressure of the small diameter tube (445). Consequently, the small diameter tube (445) securely grips the transition tube (450). The overlap (452) between the small diameter tube (445) and the transition tube (450) is approximately 1 millimeter. This leaves an exposed portion (454) of the transition tube with a length of approximately 3 millimeters or less. The signal wires (430) pass straight through transition tube (450) and into flexible body (470). The small diameter tube (445) is backfilled with silicone to secure the helical signal wires (430) in place. In one example, the silicone backfill is liquid silicone that cures with a Shore A hardness of 25.

FIG. 7 is a side view of the distal end of the small diameter tube (445), the transition tube (450) and the flexible body (470). As discussed above, the electrode array (195) includes a number of electrodes (475) disposed along the length of the flexible body (470). The electrode array (195) may also include several markers (480, 485) and/or non-active electrodes that serve as radio opaque markers to verify the position of the electrode array (195) in the cochlea. Each of the signal wires (430) terminate at one of the electrodes (475). Individual voltage signals representing sounds are transmitted along the various signal wires (430)

to the appropriate electrodes. The voltage from the electrodes (475) stimulates nearby neurons. In this example, there are active 16 electrodes in the electrode array. Consequently, there are at least 16 signal wires. A number of additional wires may also be included in the signal wires (430). In this illustrative embodiment, there are 18 signal wires.

The flexible body (470) mechanically joins the components of the electrode array (195) together while allowing for the electrode array to bend to accommodate the insertion process and to adapt to the unique geometry of a patient's cochlea. For example, the flexible body (470) may be formed from a silicon overmolding that encapsulates the electrodes (475), signal wires (430), and transition tube (450). The flexible body (470) may also include a number of molded features such as a lumen (455) and markers (480, 485). The lumen (455) is a cavity into which a stylet can be placed to guide the electrode array (195) into the desired position within the cochlea. The lumen (455) can have a variety of lengths and diameters. In this example, the lumen (455) extends past the most distal electrode in the electrode array (195). The proximal end of the lumen (455) is reinforced with a polytetrafluoroethylene tube. The lumen (455) is offset from small diameter tube (445) and transition tube (450). For example, the lumen (455) may be offset from the transition tube (450) by approximately 0.5 millimeters.

Figure 8:
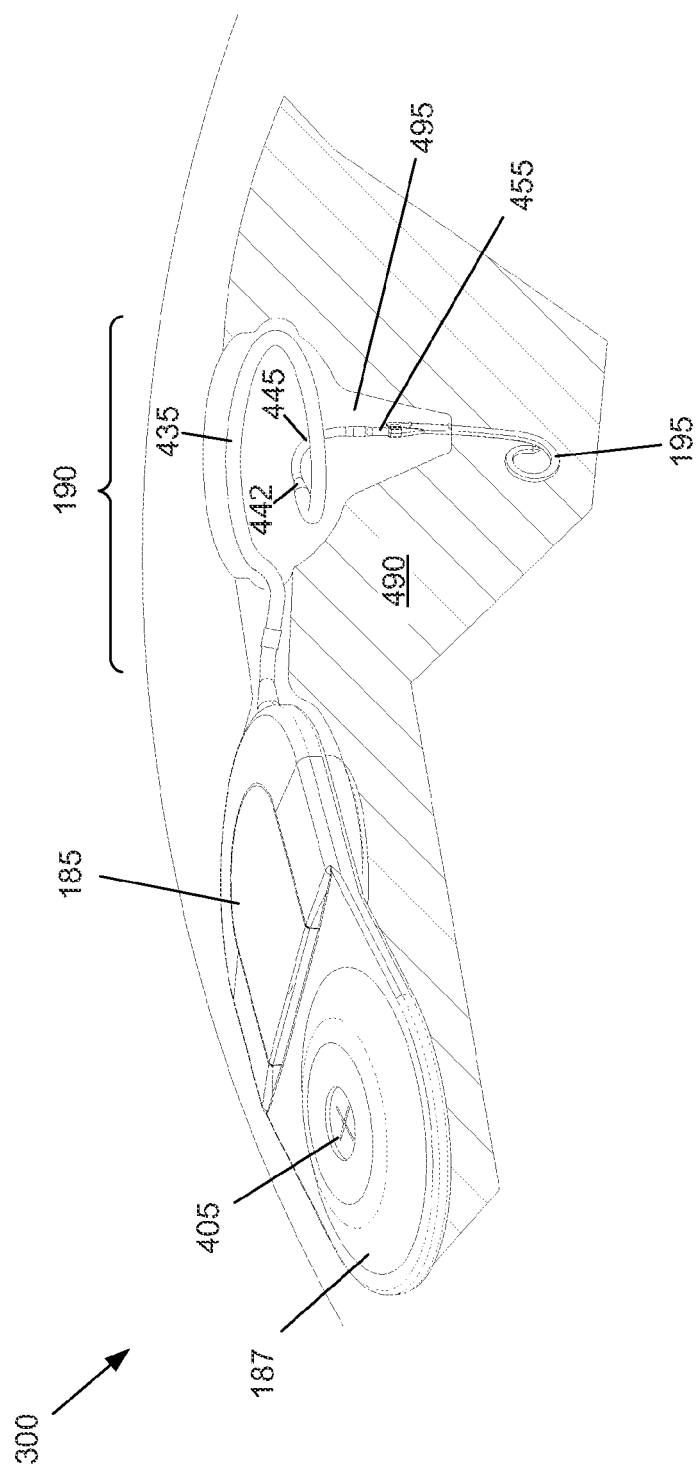
FIG. 8 is a partially cut away perspective view of internal components of a cochlear implant disposed in a patient, according to one example of principles described herein.

FIG. 8 is a diagram of the internal components (300) surgically implanted into a patient. The antenna (187) and processor (185) are positioned beneath the skin of the patient. In some examples, a facial recess (495) can be formed in the mastoid bone (490) to reduce the profile of the processor and secure it in place. The electrode array (195) is placed into the cochlea and the lead body (435, 445) is coiled into position within the facial cavity (495) in the mastoid bone (490). As discussed above, the cochlear lead (190) is designed to be flexible and have a minimal cross section. This allows the surgeon to position the cochlear lead (190) using minimal force. The flexibility of the cochlear lead (190) also allows it to more easily be retained in place because is generates minimal restoring spring force after deflection. The reduced spring forces may allow for better bio-adaptation of the surrounding tissues. In some embodiments, the surgeon may suture and/or pack the surrounding tissues into the facial recess (495) formed in the mastoid (490). Securing the cochlear lead (190) significantly contributes to the stability of the electrode array (195) within the cochlea. Further, because the cochlear lead (190) is flexible enough to be coiled within the facial recess (495), the surgeon has significant flexibility in routing the lead body and positioning the cochlear electrode. Further, the curvature and flexibility of the cochlear lead (190) mechanically decouples exterior forces and deflections from the electrode array (195). For example, an external impact to the head of the patient in the area of the processor (185) would not ordinarily lead to a shift in the position in the electrode array (195) because of the flexibility and curvature of the cochlear lead (190).

According to one embodiment, the curvature of the cochlear lead (190) primarily occurs in the large diameter tube (435), with the overlap joint (442) between the large diameter tube (435) and small diameter tube (445) remaining relatively straight. Because of the dual wall thickness at the overlap joint (442), the joint may be somewhat stiffer than the large diameter tube (435) or the small diameter tube (445). The tapered transition between the overlap joint (442) and the small diameter tube (445) minimizes kinking of the tubes near the overlap joint (442). The more flexible small diameter tube (445) bends toward the cochlea to allow for minimal stresses after the electrode array (195) is placed in the cochlea.

Figure 9A:
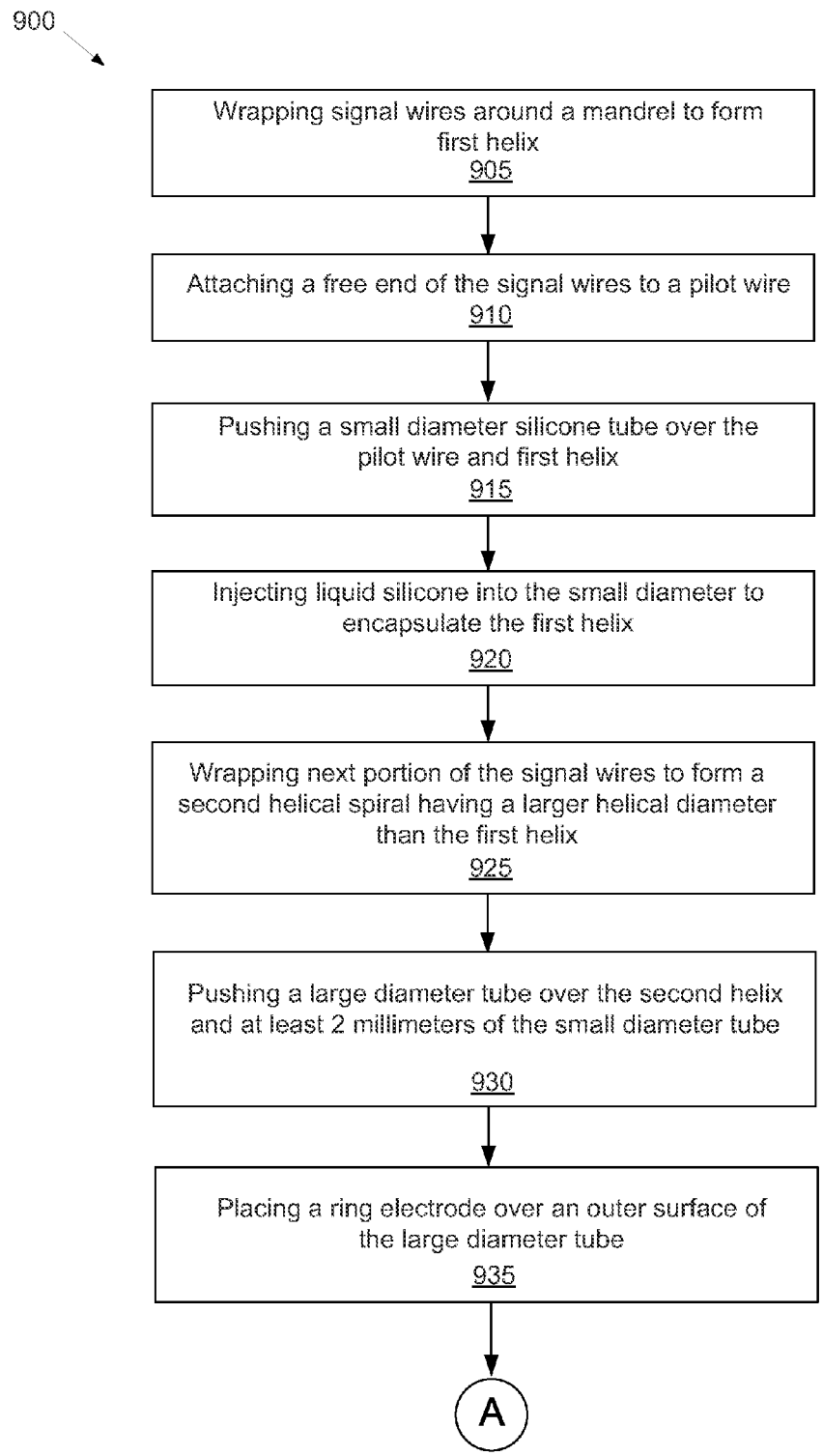
FIGS. 9A and 9B show a flowchart of a method for forming an atraumatic electrode lead, according to one example of principles described herein.
Figure 9B:
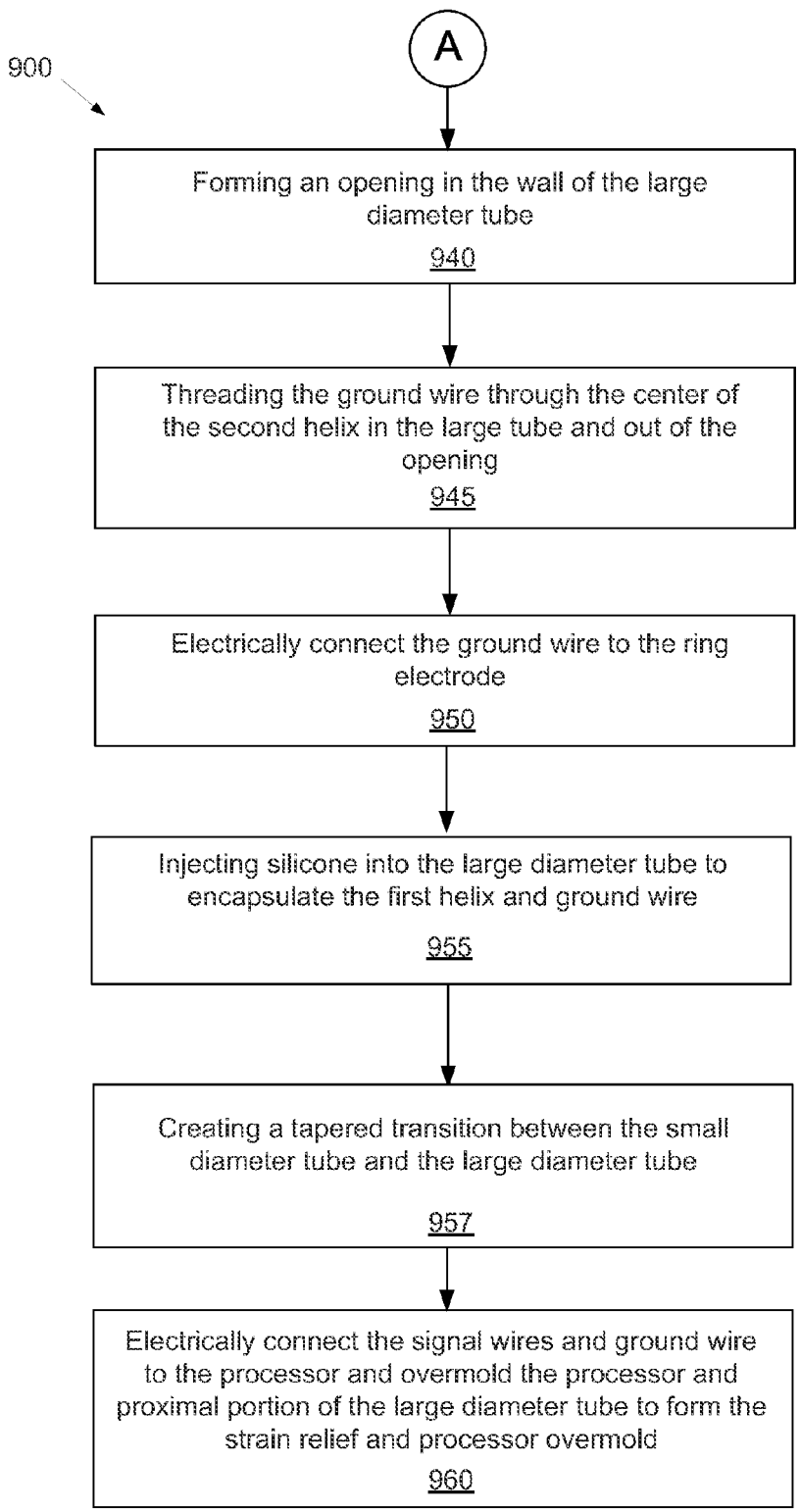

FIGS. 9A and 9B show a flow chart of an illustrative method (900) for forming a lead body of a cochlear lead. The method includes wrapping signal wires around a mandrel to form first helix (step 905). For example, the first helix may be formed by wrapping the signal wires around a 0.3 mm to 0.5 mm mandrel with a 1-2 millimeter pitch. A free end of the signal wires is attached to a pilot wire (step 910). The small diameter silicone tube is placed over the pilot wire and the first helix (step 915) and liquid silicone is injected into the small diameter tube to encapsulate the first helix (step 920). The next portion of the signal wires are wrapped to form a second helix having a larger helical diameter than the first helix (step 925). For example, the signal wires may be wound with a 1-2 millimeter pitch around mandrel with a diameter of 0.5 millimeters to 0.7 millimeters. A large diameter tube is placed over the second helix and at 1 to 2 millimeters of the small diameter tube (step 930). A ring electrode is placed over an outer surface of the large diameter tube (step 935).

Continuing with the flowchart at the top of FIG. 9B, to connect the ring electrode to the processor, an opening is formed in the wall of the large diameter tube (step 940) and a ground wire that has previously been formed into a helix is threaded through the center of the second helix in the large tube and out of the opening (step 945). The ground wire is electrically connected to the ring electrode (step 950). For example, the ground wire may be laser welded or resistance welded to the ring electrode. Silicone is injected into the large diameter tube to encapsulate the wires (step 955). A tapered transition is formed between the small diameter tube and the large diameter tube (step 957). For example, liquid silicone could be deposited over the joint, shaped, and cured. The signal wires and ground wire are electrically connected to the processor and the processor and the proximal portion of the large diameter tube are overmolded to form the strain relief and processor overmold (step 960).

The steps described above are only illustrative examples. The steps in the method may be combined, eliminated, reordered, or additional steps may be added. The order in which the steps are presented is not limiting. For example, the steps of forming an opening the wall of the large diameter tube and threading the ground wire spiral through large diameter tube could be performed in reverse order. Examples of additional steps include forming tapering transitions between the ring electrode and the outer surface of the large diameter tube.

In sum, flexural geometries in wires between electrodes in a cochlear electrode array reduce the tendency of the electrode array to uncoil/open after molding. This reduces the amount of encapsulation material on the apical portion of the electrode array and allows the electrode array to be produced using a single shot mold. The thinner electrode array can be more easily inserted into a mid-scalar position with reduced trauma to the cochlea.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear implant comprising:
a processor:
an array of electrodes disposed along a flexible body; and
a lead body connecting the processor to the array of electrodes, the lead body comprising:
a first tube having a first outside diameter;
a second tube having a second outside diameter smaller than the first diameter, a portion of the second tube being disposed within the first tube, wherein the second tube extends outside of the first tube toward the flexible body; and
wires passing through the first tube and the second tube, the wires comprising a helically coiled portion;
wherein the lead body comprises an additional length between the processor and the array of electrodes to accommodate formation of a loop in the lead body during implantation to absorb force.

2. The implant of claim 1, in which at least 1 millimeter of the second tube is disposed within the first tube to form a joint between the first tube and second tube.

3. The implant of claim 1, in which the first tube comprises an outside diameter of between 1 to 2 millimeters and an inside diameter of between 0.5 and 1 millimeters.

4. The implant of claim 3, in which the second tube comprises a nominal outside diameter larger than the nominal inside diameter of the first tube.

5. The implant of claim 1, in which the first tube and second tube comprise silicone with Shore A hardness of approximately 30 to 70.

6. The implant of claim 1, in which the lead body further comprises a tapered transition between the first tube and the second tube.

7. The implant of claim 6, in which the tapered transition comprises tapered silicone with a Shore A hardness of approximately 25.

8. The implant of claim 1, further comprising a lumen disposed in the electrode array, the lumen being offset from the lead body.

9. The implant of claim 1, in which a first part of the helically coiled portion is disposed in the first tube and a second part of the helically coiled portion is disposed the second tube, and the first tube and second tube are backfilled with silicone.

10. The implant of claim 1, further comprising an extracochlear ring electrode disposed over the first rube and electrically and mechanically coupled to the processor by ground wire passing down the center of the helically coiled portion of the wires to the ring electrode.

11. A method for forming the cochlear implant of claim 1, the method comprising:
wrapping a plurality of wires around a mandrel to form a first helix;
attaching a free end of each of the wires to a pilot wire;
installing a small diameter silicone tube over the pilot wire and first helix;
injecting liquid silicone into the small diameter tube to encapsulate the first helix;
wrapping next portion of the wires to form a second helix having a larger diameter than the first helix; and
installing a large diameter tube over the second helix and at least 2 millimeters of the small diameter tube.

12. The method of claim 11, further comprising creating a tapered transition between the small diameter tube and large diameter tube using silicone.

13. The method of claim 11, further comprising:
placing a ring electrode over an outer surface of the large diameter tube;
forming an opening in the wall of the large diameter tube;
threading ground wire through the center of the second helix in the large tube and out of the opening; and
laser welding the ground wire to the ring electrode.

14. The method of claim 13, further comprising injecting silicone into the large diameter tube to encapsulate the second helix and ground wire.

15. A cochlear implant comprising:
a processor;
an array of electrodes disposed along a flexible body; and
a lead body connecting the processor to the array of electrodes, the lead body comprising:
a first tube having a first outside diameter;
a second tube having a second outside diameter smaller than the first diameter, a portion of the second tube being disposed within the first tube; and
wires passing through the first tube and the second tube, the wires comprising a helically coiled portion;
in which the lead body further comprises a third tube, an internal portion of the third tube molded into the flexible body and an external portion extending out of the flexible body, in which the wires pass linearly through the third tube.

16. The implant of claim 15, in which a distal portion of the second tube is disposed over the external portion of the third tube to form a transition between the second tube and third tube, in which a distance between a distal end of the second tube and the flexible body is 3 millimeters or less.

17. The implant of claim 15, in which the first tube connects the processor and the second tube, the second tube is connects the first tube and the third tube, and the third tube connects the second tube and the electrode array.

18. A cochlear implant comprising:
a processor comprising an overmold and a strain relief;
an array of electrodes disposed along a flexible body having a lumen there through;
a lead body connecting the processor to the array of electrodes, the lead body comprising:
a first tube having an outer diameter of less than 2 millimeters and a Shore A hardness between 50 and 70;
a second tube having an outer diameter of less than 1 millimeter and a Shore A hardness between 50 and 70, a portion of the second tube disposed within the first tube;
a tapered transition between the first tube and second tube of silicone with a Shore A hardness less than 30;
a third tube extending between the second tube and the flexible body;
a platinum iridium wire bundle passing through the first tube, second tube, and molded straight portion, the wire bundle forming a helix having a first helical diameter in the first tube and a second helical diameter in the second tube and being straight through the third tube;
a ring electrode disposed over the first tube;
a ground wire passing through the center of the wire bundle helix in the first tube, the ground wire electrically connecting the ring electrode to the processor; and
silicone disposed within the first tube and second tube, the silicone encapsulating the wire bundle and ground wire;
in which the lumen through the flexible body is offset from the lead body.

19. A cochlear implant comprising:
a processor;
an array of electrodes disposed along a flexible body; and
a lead body connecting the processor to the array of electrodes, the lead body comprising:
  a first tube having a first outside diameter;
  a second tube having a second outside diameter smaller than the first diameter, a portion of the second tube being disposed within the first tube, wherein the second tube extends outside of the first tube toward the flexible body; and
  wires passing through the first tube and the second tube, the wires comprising a helically coiled portion;
in which:
the portion of the second tube disposed within the first tube forms an overlap joint; and
the first tube and the second tube extend in opposite directions from the overlap joint with enough length and flexibility to form a coil during implantation that includes the overlap joint and mechanically decouples the processor from the array of electrodes along the flexible body.

20. A method of implanting a cochlear implant that comprises:
a processor;
an array of electrodes disposed along a flexible body; and
a lead body connecting the processor to the array of electrodes, the lead body comprising:
  a first tube having a first outside diameter;
  a second tube having a second outside diameter smaller than the first diameter, a portion of the second tube being disposed within the first tube, wherein the second tube extends outside of the first tube toward the flexible body; and
  wires passing through the first tube and the second tube, the wires comprising a helically coiled portion,
where the portion of the second tube disposed in the first tube forms an overlap joint,
the method comprising:
  forming a loop at the overlap joint to mechanically decouple the processor from the array of electrodes along the flexible body.

21. The method of claim 20, further comprising: forming a hollow in bone, where the hollow contains the loop after implantation of the implant.

\* \* \* \* \*